United States Patent [19]
Bower et al.

[11] Patent Number: 5,989,899
[45] Date of Patent: Nov. 23, 1999

[54] OVERSIZED CELLULASE COMPOSITIONS FOR USE IN DETERGENT COMPOSITIONS AND IN THE TREATMENT OF TEXTILES

[75] Inventors: Benjamin S. Bower, Pacifica; Kathleen A. Clarkson, San Francisco; Edmund A. Larenas, Moss Beach; Michael Ward, San Francisco, all of Calif.

[73] Assignee: Genencor International, Inc., Rochester, N.Y.

[21] Appl. No.: 08/774,065

[22] Filed: Dec. 23, 1996

[51] Int. Cl.⁶ ................................................ C12S 11/00
[52] U.S. Cl. .................................... 435/263; 435/264
[58] Field of Search ................................ 435/263, 264

[56] References Cited

U.S. PATENT DOCUMENTS 5,298,405  3/1994  Nevelainen et al. .................... 435/209

FOREIGN PATENT DOCUMENTS

| 94/07983 | 4/1994 | WIPO . |
|---|---|---|
| WO 94/07998 | 4/1994 | WIPO . |
| WO 94 21801 | 9/1994 | WIPO . |
| WO 96 16177 | 5/1996 | WIPO . |
| WO 97/01629 A1 | 1/1997 | WIPO . |

OTHER PUBLICATIONS

Hatsutori, M., et al., (1997) Chem. Abst. 126:294536m.
Saloheimo, M., et al. (1988) Gene 63, 11–21.
Abuchowski, A. et al., "Alteration of Immunological Properties of Bovine Serum Albumin by Covalent Attachment of Polyethylene Glycol," *The Journal of Biological Chemistry*, vol. 252, No. 11, Issue of Jun. 10, pp. 3578–3581, 1977.
Abuchowski, A. et al., "Effect of covalent Attachment of Polyethylene Glycol on Immunogenicity and Circulating Life of Bovine Liver Catalase," *The Journal of Biological Chemistry*, vol. 252, No. 11, Issue of Jun. 10, pp. 3582–3586, 1977.
Cosgrove, et al., "Autolysis and extension of isolated walls from growing cucumbdr hypocotuyls," *J. of Experimental Botany*, vol. 45, Special Issue, pp. 1711–1719, Nov. 1994.
Delgado, C. et al., "Coupling of Poly(ethylene glycol) to Albumin under Very Mild conditions by Activation with Treasyl Chloride; Characterization of the Conjugate by Partitioning in Aqueous Two–Phase systems," *Biotechnology and Applied Biochemistry*, vol. 12, pp. 119–128, (1990).
Fortier, G. et al., "Surface modification of horseradish peroxidase with poly (ethylene glycols)s of various molecular masses," *Biotechnol. Appl. Biochem.*, vol. 17, pp. 115–130 1993.
Inada, Y. et al., "Biomedical and biotechnological applications of PEG–and PM–modified proteins," *Focus*, Tibtech Mar. 1995, vol. 13, pp. 86–91.
Inada, Y. et al., "Polyethylene Clycol(PEG)–Protein Conjugates; Application to Biomedical and Biotechnological Processes," *Journal of Bioactive and Compatible Polymers*, vol. 5, Jul. 1990, pp. 343–365.
Jackson, C. et al., "Synthesis, Isolation, and Characterization of Conjugates of Ovalbumin with Monomethoxypolyethylene Glycol Using Cyanuric chloride as the Coupling Agent," *Analytical Biochemistry*, vol. 165, 1987, pp. 114–127.
Khan, S. et al., "Polyethylene glcol–modified subtilisin forms micropraticulate suspensions in organic solvents," *Enzyme Microb. Technol.*, 1992, vol. 14, Feb., pp. 96–101.
Linder, M. et al., "Characterization of a Double Cellulose–binding Domain,." *The Journal of Biological Chemistry*, V. 271 (35), pp. 21268–21272, Aug. 30, 1996.
Luderer, M. et al., "A re–appraisal of Multiplicty of endoglucanase from *Trichodema reesei* using monoclonal antibodies and plasma desorption mass spectrometry," *Biochimica et aBiophysica Acta*, V. 1076 (1991) pp. 427–434.
McGennis, K. et al., Dimerization of *Thermomonospora fusca* β1,4–Endoglucanase E2†, *Biochemistry*, 1993, V. 32, pp. 8146–8150.
Park, W. et al., "Development of Effective Modified Cellulase for Cellulose Hydrolysis Process," *Biotechnology and Bioengineering*, vol. 45, pp. 366–373 (1995)8.
Plou, F. et al., "Acylation of subtilisin with long fatty acyl residues affects its activity and thermostability in aqueous medium," *FEBS Letters*, vol. 339, 194, pp. 200–204.
Yang, Z. et al., "Activity and Stability of Enzymes Incorporated into Acrylic Polymers," *J. Am. Chem Soc.*, 1995, 117, pp. 4843–4850.
Yang, Z. et al., "Synthesis of Protein–Containing polymers in Organic Solvents," *Biotechnology and Bioengineering*, vol. 45, pp. 10–17, 1995.
Zalipsky, S. et al., "Evaluation of a New Reagent for Covalent Attachment of Polyethylene Glycol to Proteins," *Biotechnology and Applied Biochemistry*, vol. 15, 1992, vol. 15, pp. 100–114.
PCT International Search Report PCT/US97/23336, Aug. 20, 1998.

*Primary Examiner*—Charles Patterson, Jr.
*Attorney, Agent, or Firm*—Christopher L. Stone

[57] ABSTRACT

The present invention relates to a modified cellulase protein which is advantageously used in the treatment of textiles. Particularly, a method for treating a cellulose containing fabric is provided comprising the steps of forming an aqueous solution comprising a cellulase composition which differs from a precursor cellulase in that it has been enlarged and contacting the aqueous solution with a cellulose containing fabric for a time and under conditions appropriate to treat the fabric. The enlarged cellulase may comprise a multimeric composition of two or more distinct cellulase units or a single cellulase which has had adhered thereto polymeric or fibrous constituents.

10 Claims, 9 Drawing Sheets

```
GGGTGGTCTGGATGAAACGTCTTGGCCAAATCGTGATCGATTGATACTCGCATCTATAAGATGGCACAGA        70
TCGACTCTTGATTCACAGACATCCGTCAGCCTCAAGCCGTTTGCAAGTCCACAAACAAGCACAAGCA          140
TAGCGTCGCAATGAAGTTCCTTCAAGTCCCTCCCTGCCCTCCCTCATACCGGCCGCCCTGGCCCAAACCAGCTGT  210
              MetLysPheLeuGlnValLeuProAlaAlaLeuIleProAlaAlaLeuAlaGlnThrSerCys
                                           ←
GACCAGTGGGCAACCTTCACTGGCAACAGTCAGCAACAACCTTTGGGAGCATCAGCCGGCT                280
AspGlnTrpAlaThrPheThrGlyAsnGlyTyrThrValSerAsnAsnLeuTrpGlyAlaSerAlaGly

CTGGATTTGGCTGCGTGACGGCGGGTATCGCTCAGCGGGCCTCCAGCGCAGACTGGCAGTGGTC              350
SerGlyPheGlyCysValThrAlaValSerLeuSerGlyGlyAlaSerTrpHisAlaAspTrpGlnTrpSer

CGGCGGGCCAGAACAACGTCAAGTCGTACCAGAACTCTCAGATTGCCATTCCCCAGAAGAGGACCGTCAAC      420
GlyGlyGlnAsnAsnValLysSerTyrGlnAsnSerGlnIleAlaIleProGlnLysArgThrValAsn

AGCATCAGCAGCATGCCCACCACTGCCAGCTGGAGCTACAGCGGGAGCAACATCCGCGCTAATGTTGCGT        490
SerIleSerSerMetProThrThrAlaSerTrpSerTyrSerGlySerAsnIleArgAlaAsnValAla

ATGACTTGTTCACCGCAGCCAACCCGAATCATGTCACGTACTCGGGAGACTACGAACTCATGATCTGgta        560
TyrAspLeuPheThrAlaAlaAsnProAsnHisValThrTyrSerGlyAspTyrGluLeuMetIleTrp agccataagaagtgaccctccctgatagtttcgactaacaacatgtcttgagGCTTGGCAAATACGGCGA        630
                                                    LeuGlyLysTyrGlyAsp
```

FIG._1A

```
TATTGGGCCGATTGGGTCCTCACAGGGAACAGTCAACGTCGGTGGCCAGAGCTGGACGCTCTACTATGGC    700
IleGlyProIleGlySerSerGlnGlyThrValAsnValGlyGlyGlnSerTrpThrLeuTyrTyrGly

TACAACGGAGCCATGCAAGTCTATTCCTTTGTGGCCCAGACCAACACTACAGCGGAGATGTCA           770
TyrAsnGlyAlaMetGlnValTyrSerPheValAlaGlnThrAsnThrThrAsnTyrSerGlyAspVal

AGAACTTCTTCAATTATCTCCGAGACAATAAAGGATACAACGCTGCAGGCCAATATGTTCTTAgtaagtc   840
LysAsnPhePheAsnTyrLeuArgAspAsnLysGlyTyrAsnAlaAlaGlyGlnTyrValLeu accctcactgtgactgggctgagtttgttgcaacgtttgctaacaaaacccttcgtatagGCTACCAATTT  910
                                                            SerTyrGlnPhe GGTACCGAGCCCTTCACGGGCAGTGGAACTCTGAACGTCGCCATCCTGGACCGCATCTATCAACTAAAACC  980
GlyThrGluProPheThrGlySerGlyThrLeuAsnValAlaSerTrpThrAlaSerIleAsn***

TGGAAACGTGAGATGTGGTGGGCATACGTTATTGAGCGAGGGAAAAAAGCATTGGATCCATTGAAGATG    1050
```

FIG. 1B

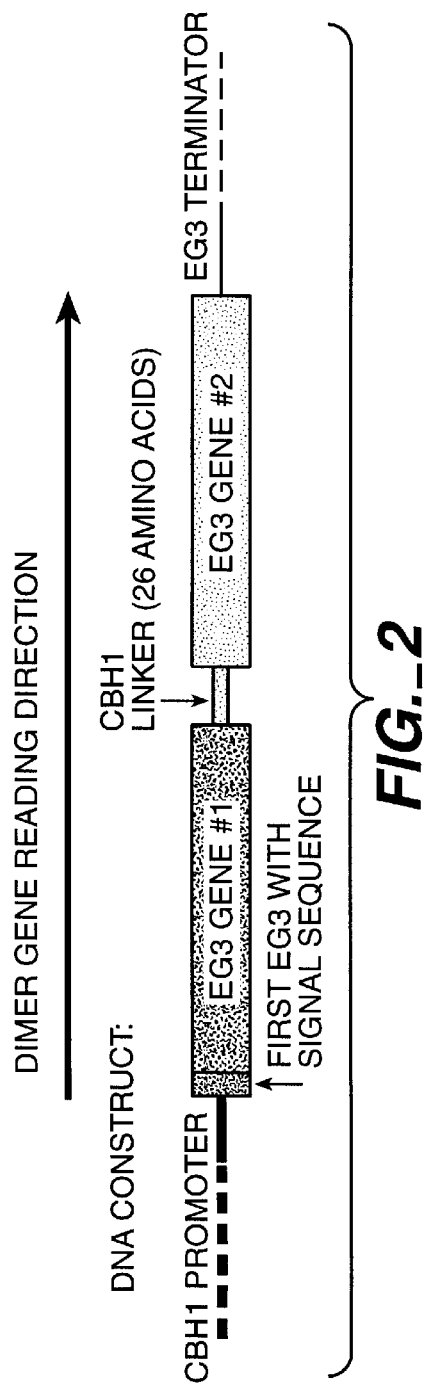
FIG._2
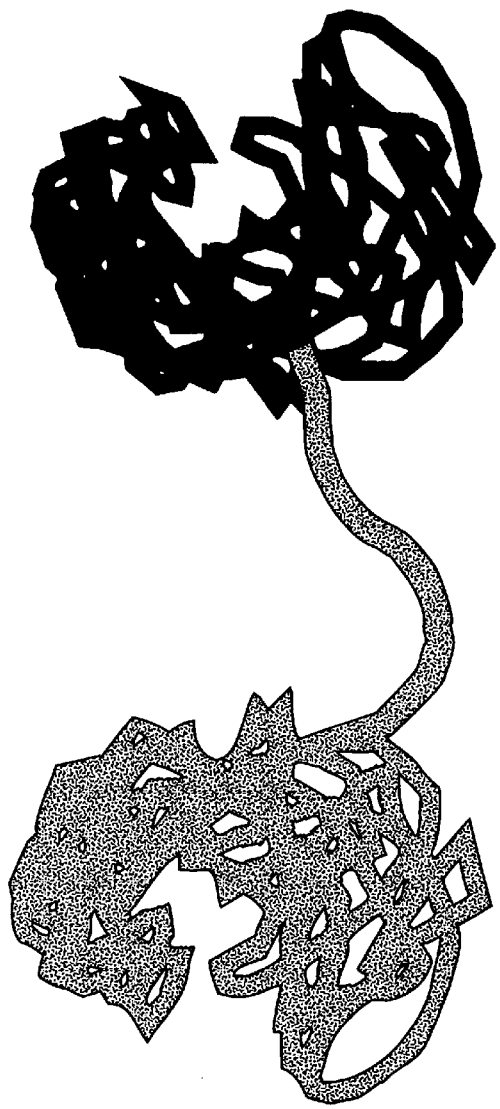
FIG._3

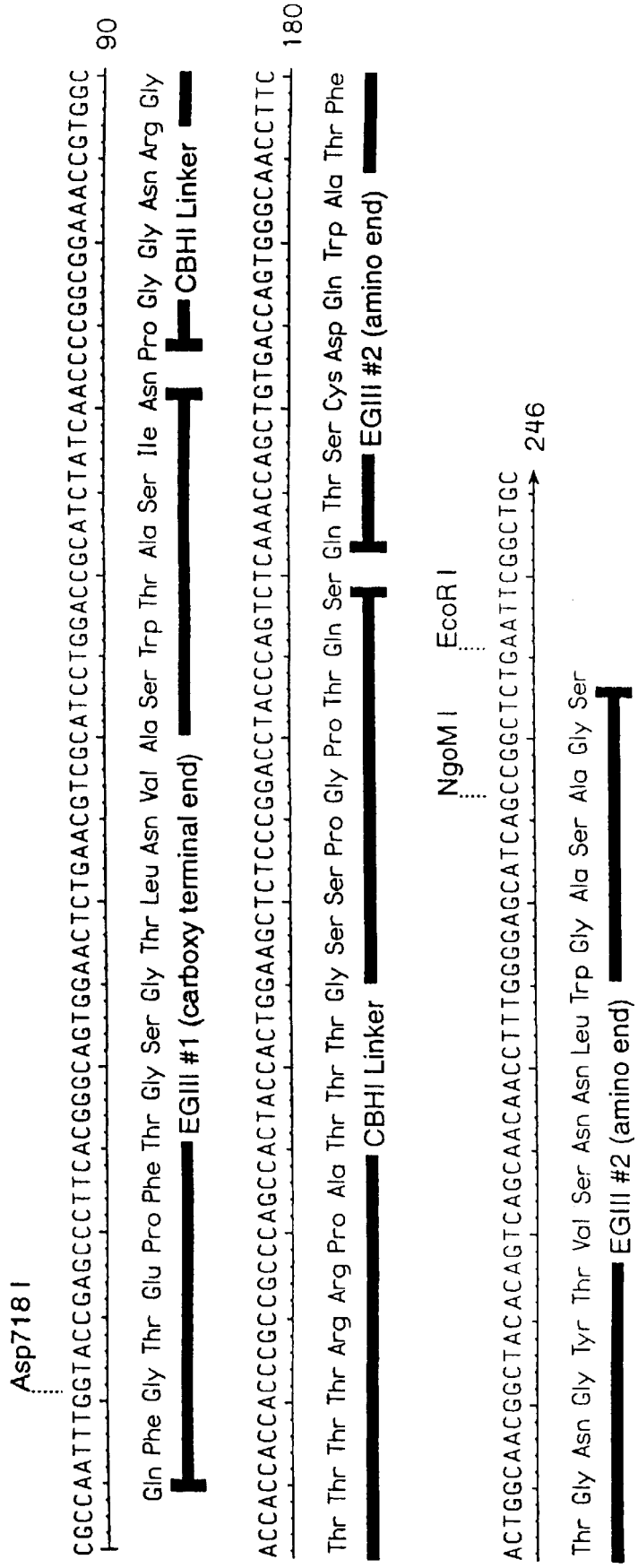
FIG._4

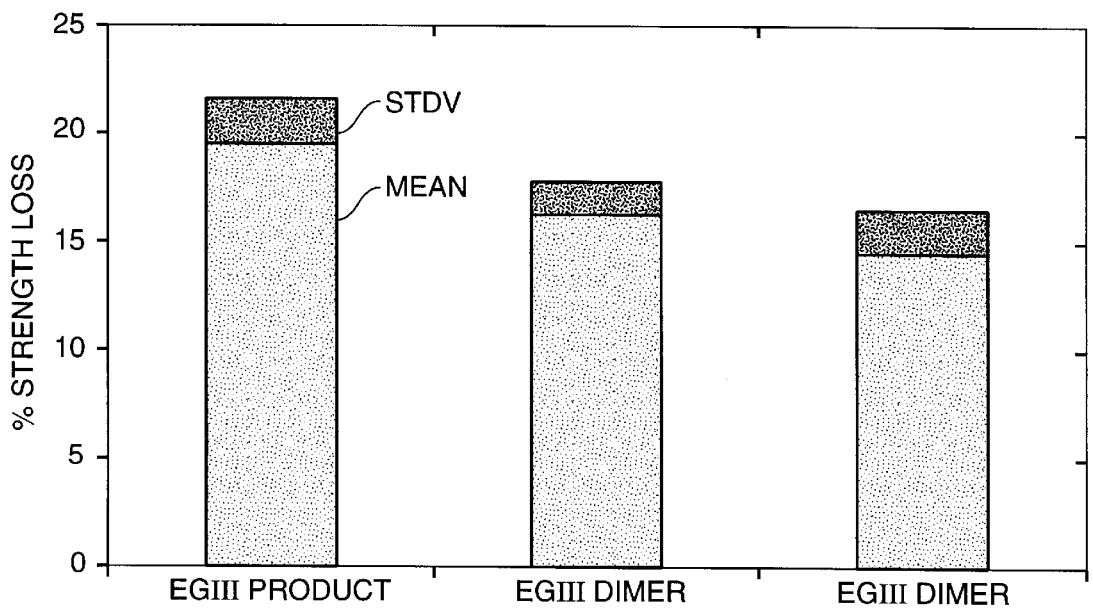
FIG._5
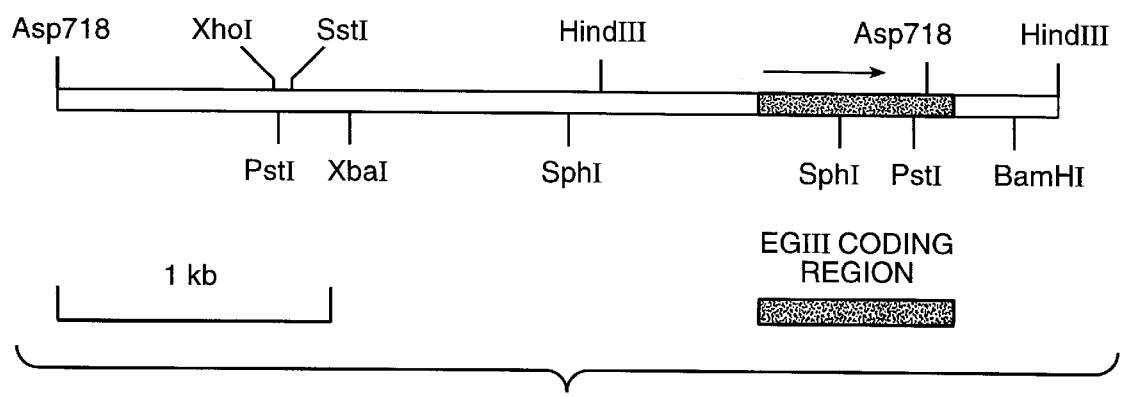
FIG._7

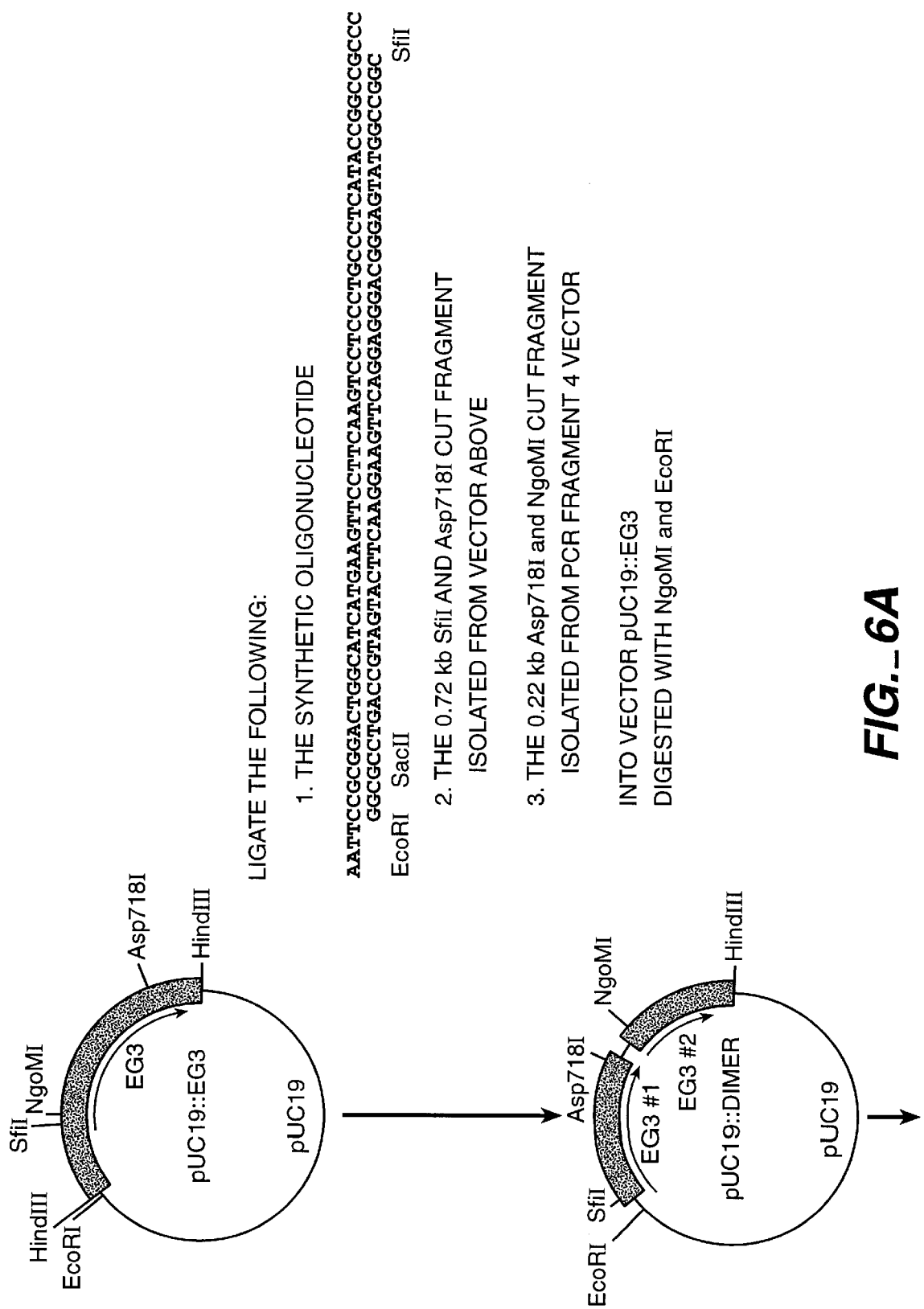
FIG._6A

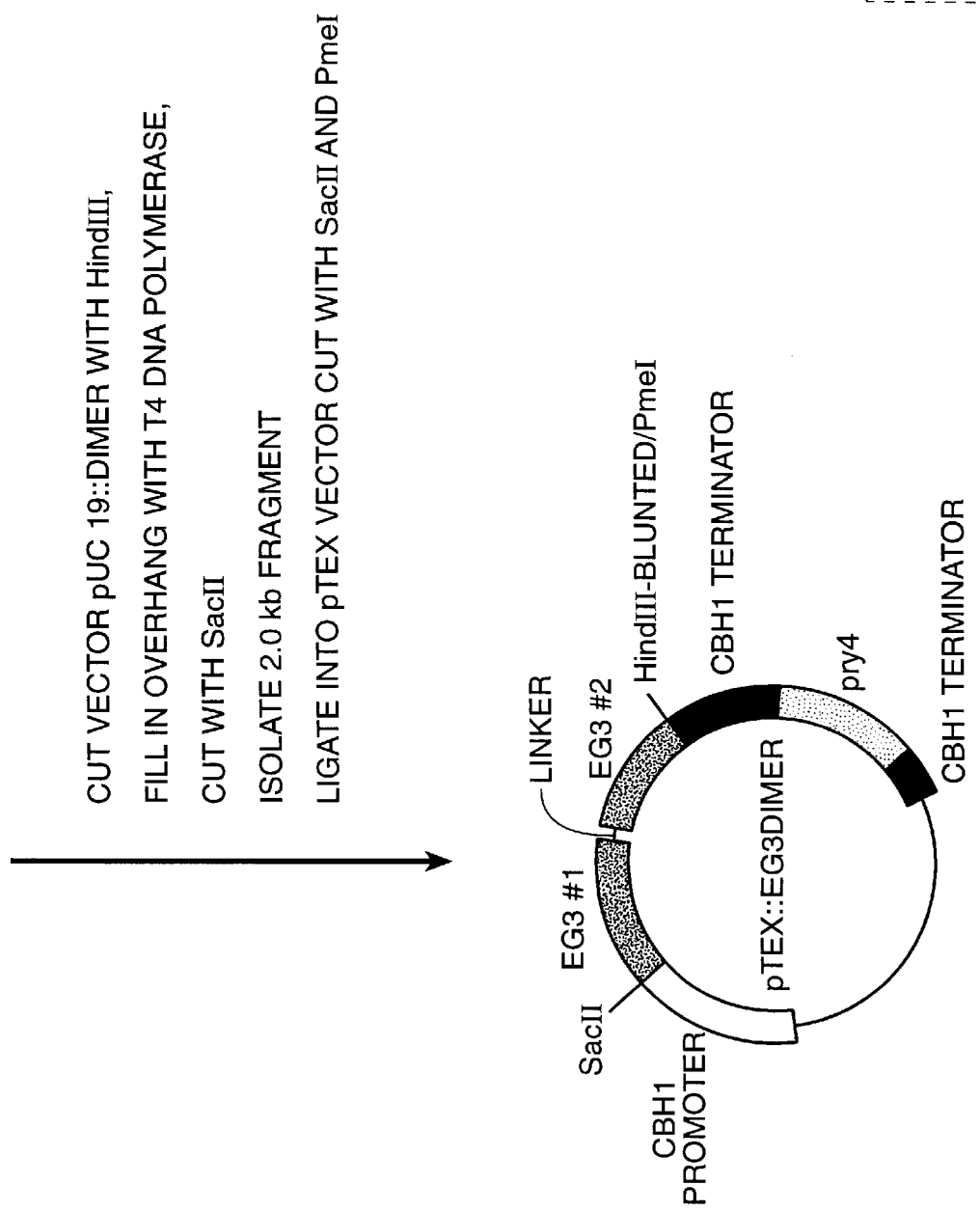

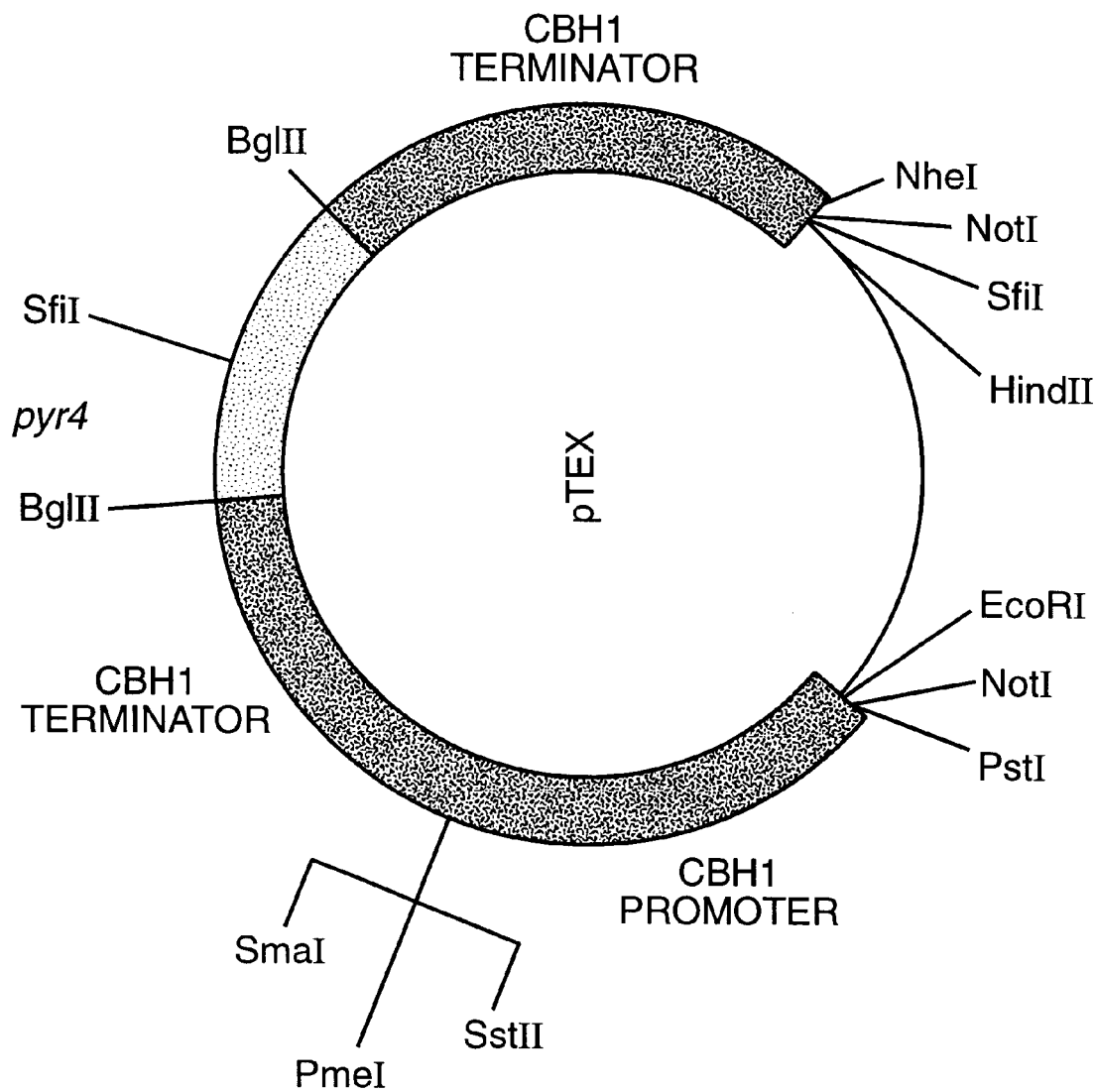
FIG._8

OVERSIZED CELLULASE COMPOSITIONS FOR USE IN DETERGENT COMPOSITIONS AND IN THE TREATMENT OF TEXTILES

FIELD OF THE INVENTION

The present invention is directed to novel cellulase compositions which have exceptional performance in detergents and in the treatment of textiles. The present invention further relates to the production of such compositions and methods of treating and/or laundering textiles utilizing such compositions, and is particularly directed to the treating or laundering of textiles with a cellulase which has been modified so as to adhere constituents thereto which increase its size and/or alter its structural properties.

STATE OF THE ART

Cellulases are enzymes which are capable of the hydrolysis of the β-D-glucosidic linkages in celluloses. Cellulolytic enzymes have been traditionally divided into three major classes: endoglucanases, exoglucanases or cellobiohydrolases and β-glucosidases (Knowles, J. et al. (1987), TIBTECH 5, 255–261); and are known to be produced by a large number of bacteria, yeasts and fungi.

Primary among the applications that have been developed for the use of cellulolytic enzymes are those involving degrading (wood)cellulose pulp into sugars for (bio)ethanol production, textile treatments like 'stone washing' and 'biopolishing', and in detergent compositions. Thus, cellulases are known to be useful in the treatment of mechanical pulp (see e.g., PCT Publication No. WO 92/16687). Additionally, cellulases are known to be useful as a feed additive (see e.g., PCT Publication No. WO 91/04673) and in grain wet milling.

Of primary importance, however, cellulases are used in the treatment of textiles, i.e., in detergent compositions for assisting in the removal of dirt or grayish cast (see e.g., Great Britain Application Nos. 2,075,028, 2,095,275 and 2,094,826 which illustrate improved cleaning performance when detergents incorporate cellulase) or in the treatment of textiles prior to sale, i.e., for improving the feel and appearance of the textile. Thus, Great Britain Application No. 1,358,599 illustrates the use of cellulase in detergents to reduce the harshness of cotton containing fabrics and cellulases are used in the treatment of textiles to recondition used fabrics by making their colors more vibrant (see e.g., The Shizuoka Prefectural Hammamatsu Textile Industrial Research Institute Report, vol. 24, pp. 54–61 (1986)). For example, repeated washing of cotton containing fabrics results in a greyish cast to the fabric which is believed to be due to disrupted and disordered fibrils, sometimes called "pills", caused by mechanical action. This greyish cast is particularly noticeable on colored fabrics. As a consequence, the ability of cellulase to remove the disordered top layer of the fiber and thus improve the overall appearance of the fabric has been of value.

Thus, cellulases have been shown to be effective in many industrial processes. Accordingly, there has been a trend in the field to search for specific cellulase compositions or components which have particularly effective performance profiles with respect to one or more specific applications. In this light, cellulases produced (expressed) in fungi and bacteria have been extensively screened and scrutinized. For example, cellulase produced by certain fungi such as Trichoderma spp. (especially *Trichoderma longibrachiatum*), have been given much attention because a complete cellulase system capable of degrading crystalline forms of cellulose is readily produced in large quantities via fermentation procedures. This specific cellulase complex has been extensively analyzed to determine the nature of its specific components and the ability of those components to perform in industrial processes. For example, Wood et al, "Methods in Enzymology", 160, 25, pages 234 et seq. (1988), disclose that complete fungal cellulase systems comprise several different enzyme classifications including those identified as exo-cellobiohydrolases (EC 3.2.1.91) ("CBH"), endoglucanases (EC 3.2.1.4) ("EG"), and β-glucosidases (EC 3.2.1.21) ("BG"). The fungal cellulase classifications of CBH, EG and BG can be further expanded to include multiple components within each classification. U.S. Pat. No. 5,475,101 (Ward et al.) discloses the purification and molecular cloning of EGIII from *Trichoderma longibrachiatum*. PCT Publication No. 94/28117 discloses the isolation and sequence of a 20–25 kD cellulase derived from *Trichoderma reesei* called EGV.

However, many components, be they from Trichoderma or other bacterial and fungal species including Humicola spp., Bacillus spp., Thermomonospora spp., and Fusarium spp. while useful in industrial processes, show suboptimal characteristics in other respects. For example, certain cellulase components provide excellent textile treatment characteristics in terms of improving feel or hand, providing a stonewashed appearance or in removing pills or fibrils from fabrics, but have the drawback of resulting in unacceptable strength loss.

Researchers have looked for alternative cellulase compositions or components which have superior characteristics. U.S. Pat. No. 5,246,853 discloses methods for treating cotton containing fabric with a cellulase composition which is free of certain exo-cellobiohydrolase components.

PCT Publication No. WO 95/24471 discloses the use of cellulases selected from the group consisting of Family 7 cellulases and variants of these cellulases comprising a core and optionally a C-terminal link consisting of 10 amino acids at most, especially cellulases having tryptophan, tyrosine or phenylalanine in position 55 and/or having a substrate binding cleft of a depth of at least 12 Angstroms. According to the Applicants, these cellulases exhibit enhanced activity in the alkaline pH range used in detergents.

PCT Publication No. WO 95/02675 discloses detergent compositions comprising two cellulases. The first has retaining type activity, preferably having catalytic activity on cellotriose at pH 8.5 corresponding to a Kcat of at least 0.01/sec, and being capable of particulate soil removal. The second has multiple domains comprising at least one non-catalytic domain attached to a catalytic domain, preferably having catalytic activity on Red Avicel 7.5 per 1 mg of a cellulase protein higher than $10^{-4}$ IU and being capable of color clarification.

PCT Publication No. WO 95/26398 discloses chemically modified cellulases which have improved performance due to modification of the pI to be at least one pH unit higher than that of the parent or native cellulase, e.g., by coupling an amine to a carboxyl group of glutamic acid or aspartic acid residues.

Multiple enzyme aggregates have been suggested for decreasing the allergenicity of the component enzyme(s) by increasing their size. For example, PCT Publication No. 94/10191 discloses oligomeric proteins which display lower allergenicity than the monomeric parent protein and proposes several general techniques for increasing the size of the parent enzyme. Additionally, enzyme aggregates have shown improved characteristics under isolated circumstances. For example, Naka et al., Chem. Lett., vol. 8, pp. 1303–1306 (1991) discloses a horseradish peroxidase aggregate prepared by forming a block copolymer via a 2-stage block copolymerization between 2-butyl-2-oxazoline and 2-methyl-2-oxazoline. The aggregate had over 200 times more activity in water saturated chloroform than did the native enzyme.

Cross-linked enzymes prepared by the addition of glutaraldehyde has been suggested as a means of stabilizing enzymes. However, cross-linking often leads to losses in activity compared to native enzyme. For example, Khare et al., Biotechnol. Bioeng., vol. 35, no. 1, pp. 94–98 (1990) disclose an aggregate of *E. coli* β-galactosidase produced with glutaraldehyde. The enzyme aggregate, while showing improvement in thermal stability at 55° C., had an activity of only 70.8% of that of the native enzyme which was, however, considered a good retention of activity after cross-linking.

To overcome these problems, researchers have developed enzymatic aggregates which comprise fusion proteins. Such fusion proteins, if expressed properly, have not been suggested as being desirable in most industrial applications, including in the treatment of textiles. Moreover, the use of cellulolytic dimers has not been shown to be particularly useful.

Despite knowledge in the art related to many cellulase compositions having applications in some or all of the above areas, there is a continued need for new cellulase compositions having improved characteristics which are useful in, for example, treating textiles, as a component of detergent compositions, in the treatment of pulp and paper, food processing, and in the conversion of biomass. Thus, while there has been significant improvements in terms of the understanding of cellulase compositions and their activities, there remains a need for alternative cellulase compositions which retain the beneficial effects of known cellulase compositions but which have significant improvements in terms of certain adverse activities such as strength loss in fabric treatment.

SUMMARY OF THE INVENTION

It is an object of the invention to provide novel cellulase compositions which have improved properties when utilized in industrial processes such as textile treatment, laundering of textiles, feed additive technology, baking and food processing, grain wet milling and biomass conversion.

It is a further object of the invention to provide novel cellulases which have reduced strength loss characteristics when utilized in the treatment of textiles.

According to the present invention, a method is provided for treating a cellulose containing fabric comprising the steps of: (a) forming an aqueous solution comprising a cellulase composition comprising a cellulase which differs from a precursor cellulase in that it has been enlarged; (b) contacting the aqueous solution with the cellulose containing fabric for a time and under conditions appropriate to treat the cellulose containing fabric.

In a preferred embodiment of the invention, the cellulase is derived from a fungal or bacterial source, most preferably a filamentous fungus or Bacillus species. Also preferably, the enlarged cellulase comprises a fusion enzyme formed by the expression of two or more cellulase genes linked together, the expression product being a cellulolytic multimer. Alternatively, the enlarged cellulase comprises a cellulase altered by the addition of polymeric or fibrous substituents to the surface of the cellulase to alter its surface properties.

An advantage of the present invention is that the cellulose containing fabric shows reduced strength loss when treated with the enlarged cellulase of the invention compared with a cellulose containing fabric treated in an identical manner except that the cellulase composition comprises the precursor cellulase instead of the enlarged cellulase.

BRIEF DESCRIPTION OF THE DRAWINGS

FIGS. 1A–1B illustrate the DNA sequence (SEQ ID NO:1) and corresponding amino acid sequence (SEQ ID NO:2) (SEQ ID NO:3) (SEQ ID NO:4) of EGIII from *Trichoderma longibrachiatum*.

FIG. 2 illustrates a schematic of a gene fusion construct to produce an EGIII dimer.

FIG. 3 illustrates a hypothetical tertiary structure for an EGIII dimer produced according to the invention illustrating the linker derived from CBHI.

FIG. 4 illustrates the sequence of a DNA segment (SEQ ID NO:5) comprising the carboxy terminal end of the EGIII gene fused to the amino terminal end of a second EGIII gene by a CBHI linker (SEQ ID NO:6).

FIG. 5 illustrates the results of comparative strength loss of a cotton containing fabric treated with the cellulase according to the invention and native EGIII.

FIGS. 6A–6B illustrate a plasmid construction schematic showing the production of a vector for expressing EGIII dimer in *Trichoderma reesei* (sythetic oligonucleotide, SEQ ID NO:7 and SEQ ID NO:8).

FIG. 7 illustrates a diagram of the portion of the genetic DNA of *Trichoderma reesei* containing the EGIII gene.

FIG. 8 illustrates a diagram of the pTEX vector.

DETAILED DESCRIPTION OF THE INVENTION

Figure 9:
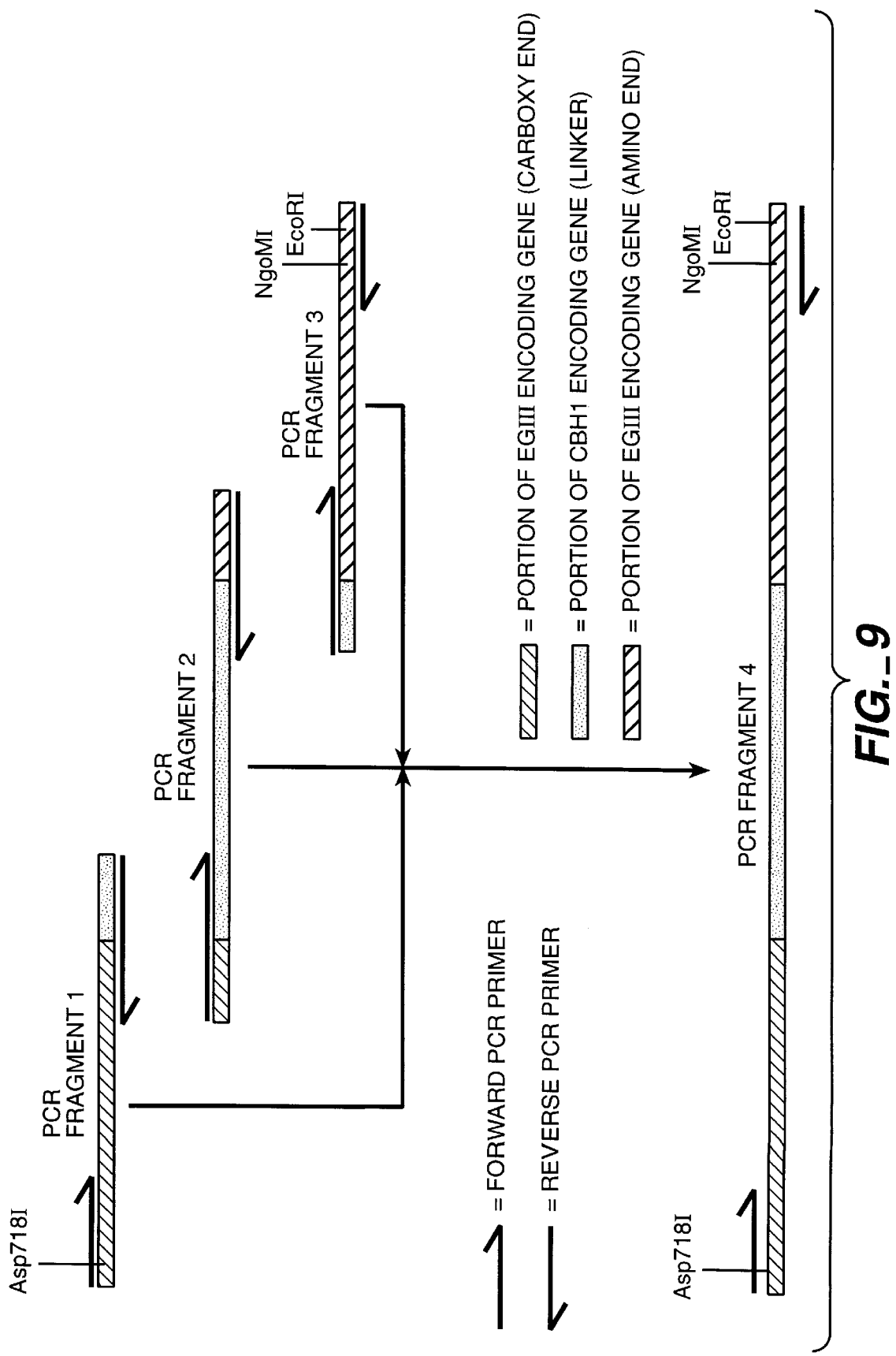
FIG. 9 illustrates a schematic diagram of the PCR strategy used to produce the EGIII dimer.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Specifically included within the definition of cellulose containing fabric is any yarn or fiber made of such materials. Cellulose containing materials are often incorporated into blends with materials such as synthetic fibers and natural non-cellulosic fibers such as wool and silk.

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Stonewashing composition" means a formulation for use in stonewashing cellulose containing fabrics. Stonewashing compositions are used to modify cellulose containing fabrics prior to presentation for consumer sale, i.e., during the manufacturing process. In contrast, detergent compositions are intended for the cleaning of soiled garments.

"Stonewashing" means the treatment of cellulose containing fabric with a cellulase solution under agitating and cascading conditions, i.e., in a rotary drum washing machine, to impart a "stonewashed" appearance to the denim. The cellulase solution according to the instant invention will functionally replace the use of stones in such art recognized methods, either completely or partially. Methods for imparting a stonewashed appearance to denim are described in U.S. Pat. No. 4,832,864 which is incorporated herein by reference in its entirety. Generally, stonewashing techniques have been applied to indigo dyed cotton denim.

"Detergent composition" means a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, Clarkson et al., U.S. Pat. No. 5,290,474 and EP Publication No. 271 004, incorporated herein by reference.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme), which peptides retain a characteristic enzyme nature of the precursor enzyme but which have altered properties in some specific aspect. For example, a cellulase derivative may have an increased pH optimum or increased temperature or oxidative stability but will retain its characteristic cellulolytic activity. Similarly, derivatives according to the present invention include a cellulose binding domain portions of which have either been added, removed or modified in such a way so as to significantly impair or enhance its cellulose binding ability. It is contemplated that derivatives according to the present invention may be derived from a DNA fragment encoding a cellulase derivative wherein the functional activity of the expressed cellulase derivative is retained. For example, a DNA fragment encoding an enlarged cellulase may further include a DNA sequence or portion thereof encoding a hinge or linker attached to the cellulase DNA sequence at either the 5' or 3' end wherein the functional activity of the encoded cellulase domain is retained. Derivative further includes chemical modification to change the characteristics of the enzyme.

"Enlarged cellulase" means a cellulase which has been manipulated to increase its mass (molecular weight), surface area or spatial volume. For example, an enlarged cellulase may be produced by manipulating a DNA encoding a parent cellulase through recombinant techniques to incorporate additional DNA, either at the 5' or 3' end or at an internal position. The expressed cellulase incorporates additional amino acids which provide additional mass (molecular weight) to the cellulase. The additional DNA may encode a distinct cellulolytic entity, i.e., forming a fusion protein comprising two or more cellulolytic catalytic sites, or may encode an additional separate non-catalytic structural region or enlarge an existing structure within the cellulase. Where the fusion protein comprises two or more distinct cellulase subunits, it would be possible to incorporate two different cellulase enzymes, for example, one or more specific endoglucanases or an endoglucanase and a cellobiohydrolase, to take advantage of different characteristics of each enzyme incorporated into the fusion protein. By way of example, endoglucanases derived from some Bacillus species have been shown to be particularly useful in anti-pilling, cleaning and anti-graying while some fungal endoglucanases have been shown to be particularly useful for color revival and abrasion. Thus, by joining a fungal endoglucanase entity with a Bacillus endoglucanase entity, it would be possible to take advantage of the features of each enzyme while simultaneously introducing other desirable attributes, e.g., reduced strength loss of textiles treated with the enlarged cellulase.

Alternativeiy, the enlarged cellulase may comprise a cross-linked cellulase multimer, e.g., two or more cellulase enzymes chemically linked via, for example, glutaraldehyde, to form a dimer or multimer. The cellulases may be the same or different enzymes. With either a cross-linked cellulase multimer or a fusion enzyme, it is desirable to orient the specific subunits in such a way that the active sites remain catalytically functional and retain access to substrate. For example, if the active sites are concealed from substrate in the modified (enlarged) cellulase, it would be expected that activity would suffer. Where the substrate comprises long insoluble polymer carbohydrate, it may be preferable to orient the enzyme in such a way so as to facilitate access of each active site to the substrate. Such active site orientation is facilitated by the use of a crystal structure or other predictive tertiary structure model which permits prediction of linking sites to optimize active site orientation.

Further alternatively, the enlarged cellulase may be formed by adhering thereto peptide or non-peptide based components which act to increase the molecular weight (mass), surface area or size. For example, pegylation is one alternative wherein high molecular weight polyethylene glycol components are adhered to the cellulase as described in, e.g., Inada et al., TIBTECH, vol. 13, (1995) pp. 86–91 and references cited therein, which disclosures are incorporated by reference. Similarly, other fibrous or polymeric constituents may be adhered to the protein surface through the many known chemical techniques for modifying amino acids. For example, polysaccharides, polypeptides, polyesters, synthetic polymers, lipids, fatty acids, chitin, chitosan and surfactants may be adhered to the protein surface to effect an alteration of the enzyme substrate interaction. Such techniques are only limited by the availability of the appropriate chemistry for attaching the specific groups to the specific protein components. Further, it is possible to incorporate synthetic amino acids, via modifying the DNA sequence of the enzyme and growing under the appropriate conditions, wherein the synthetic amino acids possess attributes which facilitate functional group attachment thereto from the polymeric or fibrous constituent. One goal of adhering constituents to the surface of the protein is to alter the surface interaction between the cellulase and the substrate. Accordingly, adding ionic substituents (i.e., cationic or anionic) will alter such interactions. Similarly uncharged but polar constituents will confer altered characteristics to the cellulase.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers. Immature cotton is significantly more amorphous than mature cotton and results in a lesser quality fabric when present due to, for example, uneven dyeing. The composition contemplated in the present invention further includes an enlarged cellulase component for use in washing of a soiled manufactured cellulose containing fabric. For example, the enlarged cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

Treating according to the instant invention comprises preparing an aqueous solution which contains an effective amount of cellulase together with other optional ingredients including, for example, a buffer, a surfactant, and/or a scouring agent. An effective amount of cellulase enzyme composition is a concentration of cellulase enzyme sufficient for its intended purpose. Thus, for example, an "effective amount" of cellulase in a stonewashing composition according to the present invention is that amount which will provide the desired effect, e.g., to produce a worn and faded look in the seams and on fabric panels. Similarly, an "effective amount" of cellulase in a composition intended for improving the feel and/or appearance of a cellulose containing fabric is that amount which will produce measurable improvements in the feel, e.g., improving the smoothness of the fabric, or appearance, e.g., removing pills and fibrils which tend to reduce the sharpness in appearance of a fabric. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be treated is added can be readily determined by the skilled artisan based on the above factors as well as the desired result. In stonewashing processes, it has generally been preferred that the cellulase be present in the aqueous treating solution in a concentration of from about 0.5 to 5,000 ppm and most preferably about 10 to 200 ppm total protein. In compositions for the improvement of feel and/or appearance of a cellulose containing fabric, it has generally been preferred that the cellulase be present in the aqueous treating solution in a concentration of from about 0.1 to 2000 ppm and most preferably about 0.5 to 200 ppm total protein.

In a preferred treating embodiment, a buffer is employed in the treating composition such that the concentration of buffer is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. The determination of the optimal pH range of the enlarged cellulases of the invention can be ascertained according to well known techniques. Suitable buffers at pH within the activity range of the enlarged cellulase are well known to those skilled in the art in the field.

In addition to cellulase and a buffer, the treating composition may optionally contain a surfactant. Suitable surfactants include any surfactant compatible with the cellulase and the fabric including, for example, anionic, non-ionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

A concentrated enlarged cellulase composition can be prepared for use in the methods described herein. Such concentrates contain concentrated amounts of the cellulase composition described above, buffer and surfactant, preferably in an aqueous solution. When so formulated, the enlarged cellulase concentrate can readily be diluted with water so as to quickly and accurately prepare enlarged cellulase preparations having the requisite concentration of each constituent. When aqueous concentrates are formulated, these concentrates can be diluted so as to arrive at the requisite concentration of the components in the cellulase solution as indicated above. As is readily apparent, such enlarged cellulase concentrates will permit facile formulation of the cellulase solutions as well as permit feasible transportation of the composition to the location where it will be used. The treating concentrate can be in any art recognized form, for example, liquid, emulsion, gel, or paste. Such forms are well known to those skilled in the art.

When a solid enlarged cellulase concentrate is employed, the cellulase composition may be a granule, a powder, an agglomerate or a solid disk. The granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the enlarged cellulase composition of the present invention as desired, including stones, pumice, fillers, solvents, enzyme activators, and anti-redeposition agents depending on the eventual use of the composition.

By way of example, stonewashing methods will be described in detail, however, the parameters described are readily modified by the skilled artisan for other applications, i.e., improving the feel and/or appearance of a fabric. The cellulose containing fabric is contacted with the enlarged cellulase containing stonewashing composition containing an effective amount of the cellulase by intermingling the treating composition with the stonewashing composition, and thus bringing the cellulase enzyme into proximity with the fabric. Subsequently, the aqueous solution containing the enlarged cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose containing fabric, in this case to produce the stonewashed effect. Generally, the enlarged cellulases of the present invention should be utilized under conditions operable for the use of the parent cellulase(s). However, such conditions are readily ascertainable by one of skill in the art. The reaction conditions effective for the stonewashing compositions of the present nvention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from about 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. While standard temperatures for cellulase usage in the art are generally in the range of 35° C. to 65° C., which conditions would also be expected to be suitable for the cellulase of the invention, the optimal temperature conditions should be ascertained according to well known techniques with respect to the specific enlarged cellulase used.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the enlarged cellulase of the invention may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally includes other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal, anti-graying and cleaning. Preferably, the cellulase in the detergent composition is employed in a concentration of from about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. The granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, nonionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyal-kylene ethers, as well as higher fatty acid alkanolamides or alkylene oxide adduct thereof, fatty acid glycerine monoesters, and the like. Suitable surfactants for use in this invention are disclosed in British Patent Application No. 2 094 826 A, the disclosure of which is incorporated herein by reference. Mixtures of such surfactants can also be used. The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent sequestering agents.

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or inorganic electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Masking Agents for Factors Inhibiting the Cellulase Activity

The cellulase composition of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators vary depending on variety of the cellulases. In the presence of proteins, cobalt and its salts, magnesium and its salts, and calcium and its salts, potassium and its salts, sodium and its salts or monosaccharides such as mannose and xylose, the cellulases are activated and their derging powers are improved remarkably.

Antioxidants

The antioxidants include, for example, tert-butyl-hydroxytoluene, 4,4'- butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1 -bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the enlarged cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising truncated cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Example 1

Cloning and Expression of an EGIII Dimer Through Recombinant DNA Techniques (1) CONSTRUCTION:

DNA comprising the EGIII encoding gene was isolated from *Trichoderma longibrachiatum* (see e.g., U.S. Pat. No. 5,475,101, the disclosure of which is incorporated herein by reference). Briefly, total DNA may be extracted from *Trichoderma longibrachiatum* strain RL-P37 and digested with various restriction enzymes. The digested DNA is subjected to agarose gel electrophoresis, transferred to a nylon membrane and hybridized with radiolabelled DNA from an M13 clone containing the 100 bp PCR fragment. From this Southern analysis, it is determined that part of the EGIII coding region resides in a 3 kb Asp718 fragment of genomic DNA. The region surrounding the EGIII encoding gene in the genomic DNA is illustrated in FIG. 7, also showing the HindIII sites which were used to prepare the DNA for the purposes of the present example.

The DNA sequence of the EGIII encoding gene (SEQ ID. NO:1) and the corresponding amino acid sequence (SEQ ID NO:2) (SEQ ID NO:3) (SEQ ID NO:4) are provided in FIG. 1. To produce a linkage between two EGIII protein molecules, it was necessary to select an appropriate linking sequence. The strategy illustrated herein is shown in FIG. 2 and comprises joining the carboxy terminal end of the first EGIII molecule with the linker region of the CBHI molecule. The EGIII-linker fusion is then joined to the amino terminus of the second EGIII molecule. The genetic engineering to accomplish this protein linkage is described below.

As shown in FIG. 9, four PCR reactions were used to create the fragment labeled "PCR fragment 4". The first three PCR reactions were made independently. These three reaction fragments have ends that are complimentary to each other allowing them to be joined in the fourth PCR reaction. Preparation of EGIII and CBHI clones may be prepared as described in U.S. Pat. No. 5,475,101 and EP Patent No. 137 280.

"PCR fragment 1" was prepared using the HindIII fragment EGIII gene clone as the DNA template. The forward primer had the sequence CGCCAATTTGGTACCGAGC-CCTTCACGGG (SEQ ID. NO:9). The reverse primer had the sequence GCCACGGTTTCCGCCGGGGTTGATA-GATGCGGTCCAGG (SEQ ID NO:10). After amplification a fragment of 90 bases was created. The DNA fragment was run out in NuSieve Agarose, cut from the gel and recovered.

"PCR fragment 2" was prepared using the CBH 1 gene clone as the DNA template . The forward primer had the sequence CCTGGACCGCATCTATCAACCCCGGCG-GAAACCGTGGC (SEQ ID NO:11). The reverse primer had the sequence CCACTGGTCACAGCTG-GTTTGAGACTGGGTAGGTCCGGG (SEQ ID NO:12). After amplification a fragment of 119 bases was created. The DNA fragment was run out in NuSieve Agarose, cut from the gel and recovered.

"PCR fragment 3" was prepared using the HindIII fragment EGIII gene clone as the DNA template. The forward primer had the sequence CCCGGACCTACCCAGTCT-CAAACCAGCTGTGACCAGTGG (SEQ ID NO:13) The reverse primer had the sequence GCAGCCGAATTCA-GAGCCGGCTGATGCTCC (SEQ ID NO:14). After amplification, a fragment of 114 bases was created. The DNA fragment was run out in NuSieve Agarose, cut from the gel and recovered.

"PCR fragment 4" was prepared by combining "PCR fragments 1, 2 and 3" in the same reaction, the resulting sequence being used as the DNA template. The forward primer has the sequence CGCCAATTTGGTACCGAGC-CCTTCACGGG (SEQ ID NO:15). The reverse primer had the sequence GCAGCCGAATTCAGAGCCGGCTGAT-GCTCC (SEQ ID NO:16). After amplification a fragment of 246 bases was created. The PCR reaction product was purified using Qiaquick PCR purification kit (Qiagen Inc., Chatsworth Calif.) following the instructions of the manufacturer. The PCR reaction product was then restriction digested with the enzymes Asp718 I and EcoR I according to manufacturers instructions. After digestion, a fragment of approximately 225 bases was created. The DNA fragment was run out in NuSieve Agarose, cut from the gel, recovered and ligated into a pUC19 vector that was cut with the same restriction endonucleases. The sequence of the created "PCR fragment 4", before the restriction digest step is given in FIG. 4.

As shown in FIG. 6, the pUC19 vector having the HindIII fragment of *Trichoderma longibrachiatum* DNA comprising the EGIII gene was used to produce the expression vehicle for the dimer. As described in FIG. 6, a synthetic oligonucleotide is created which is then ligated to the 0.72 kb Sfil and Asp718I fragment isolated from the pUC19::EG3 vector and the 0.22 kb Asp718I and NgoM1 fragment isolated from PCR fragment 4. The formed fragment is then inserted into the pUC19::EG3 vector to form the pUC19::dimer vector.

For expression of the dimer, the plasmid pTEX is constructed following the methods of Sambrook et al. (1989) (illustrated in FIG. 8; see PCT Publication No. WO 96/23928 for a complete description of the preparation of the pTEX vector, which discussion is herein incorporated by reference). The plasmid is designed as a multi-purpose expression vector for use in the filamentous fungus *Trichoderma longibrachiatum*. The expression cassette has several unique features that make it useful for this function. Transcription is regulated using the strong CBHI promoter and terminator sequences for *T. longibrachiatum*. The *T. longibrachiatum* pyr4 selectable marker gene has been inserted into the CBHI terminator and the whole expression cassette can be excised utilizing the unique NotI restriction site or the unique NotI and NheI restriction sites. Thus, while pTEX is a preferred expression cassette for the present example, it is merely an example of one of many suitable expression cassettes which have similarly convenient characteristics.

As shown in FIG. 6, vector pUC19:dimer is cut with HindIII and the overhangs filled in with T4 DNA polymerase, cut with SacII and a 2.0 kb fragment isolated. This fragment is then ligated into the pTEX vector cut with SacII and PmeI.

The dimer expression vector contained the strong CBHI promoter to drive expression of the artificial EGIII dimer gene. The stop codon of the second EGIII gene is followed by almost 300 bases of EGIII terminator. The gene pyr4 was used as selectable marker for transformation into Trichoderma.

(2) TRANSFORMATION AND SCREENING

The vector created above was used to transform a strain of *T. longibrachiatum* that had been previously deleted for four cellulase genes: CBHI, CBHII, EGI and EGII (see e.g., U.S. Pat. No. 5,472,864). Stable transformants were grown in shake flasks and assayed for endoglucanase activity using a RBB-CMC assay. The four highest producing transformants, as measured by endoglucanase activity, were grown in 15 L fermentors. The fermentation broth was harvested for analysis. On an SDS-PAGE gel a new protein band was observed at the predicted dimer size of about 50 KD. This new protein was the most prevalent protein as estimated by comassie stain. The untransformed control strain did not show such a protein band at about 50 KD. Furthermore, the 50 KD band reacts positively to a western blot probed with EGIII antibody. Accordingly, the transformed strains produce a new novel EGIII dimer enzyme as its major fermentation product.

Example 2

Comparative Strength Loss

This example studies the ability of the inventive cellulase compositions to effect less strength loss than its parent enzyme. This example employs an aqueous cellulase solution maintained at pH 5 to reflect the optimal pH of EGIII produced from a genetically altered strain of *Trichoderma longibrachiatum* produced as described in, for example, the methods provided in U.S. Pat. Nos. 5,328,841, 5,472,864 and 5,475,101. Specifically, in this example, the first cellulase analyzed was a composition comprising wild type EGIII. The second cellulase analyzed was the EGIII dimer described in Example 1.

The cellulase compositions were tested for their effect on cotton-containing fabric during stonewashing of dyed denim and the strength loss of the corresponding fabrics measured. The stonewashed denim fabrics were prepared using an industrial washer and dryer under the following conditions:

Citrate/phosphate buffer @ pH 5

38 L total volume

120–135 degrees Celsius

Six pair of denim pants with an equal weight of ballast 1 hour run time

15–30 ppm EGIII or EGIII dimer, dosed to obtain equivalent abrasion of fabric.

Strength loss was measured by determining the tensile strength in the fill direction (FTS) using an Instron Tester and the results compared to the FTS of the fabric treated with the same solution with the exception that no cellulase was added. The results of this analysis are reported as percent strength loss which is determined as follows:

$$\% \text{ Strength Loss} = 100 \times \left[1 - \left(\frac{FTSx}{FTSy}\right)\right]$$

Where FTSx is the fill direction tensile strength with cellulase and FTSy is the fill direction tensile strength without cellulase.

The results of this analysis are shown in FIG. 5 which illustrates that textiles treated with the enlarged cellulase (EGIII dimer) had significantly less strength loss than those treated with the parent EGIII cellulase when dosed with enzyme at an amount so as to obtain equal abrasion.

We claim:

1. A method for treating cellulose containing fabric comprising the steps of:
   (a) forming an aqueous solution comprising a cellulase composition comprising a cellulase which differs from a precursor cellulase in that it comprises a fusion protein having at least two cellulolytic catalytic sites; and
   (b) contacting said aqueous solution with said cellulose containing fabric for a time and under conditions appropriate to treat said cellulose containing fabric.

2. The method according to claim 1, wherein said cellulose containing fabric shows reduced strength loss compared with a cellulose containing fabric treated in an identical manner except that said cellulase composition comprises a precursor cellulase instead of said enlarged cellulase.

3. The method according to claim 1, wherein said cellulase is derived from a fungal, bacterial or plant source.

4. The method according to claim 3, wherein said cellulase is derived from a filamentous fungus or a Bacillus sp.

5. The method according to claim 4, wherein said cellulase is derived from Bacillus spp., Trichoderma spp., Humicola spp., Fusarium spp., or Thermomonospora spp.

6. The method according to claim 5, wherein said cellulase is derived from *Trichoderma longibrachiatum*.

7. The method according to claim 6, wherein said cellulase is derived from EGIII.

8. The method according to claim 1, wherein said cellulase comprises a multimer of said precursor cellulase.

9. The method according to claim 8, wherein said multimer comprises an EGIII component.

10. The method according to claim 9, wherein said multimer comprises a dimer of EGIII linked by the CBHI linker sequence.

* * * * *

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
      (A) LENGTH: 1050 base pairs
      (B) TYPE: nucleic acid
      (C) STRANDEDNESS: single
      (D) TOPOLOGY: linear (xi) SEQUENCE DESCRIPTION: SEQ ID NO:1:

```
GGGTGGTCTG GATGAAACGT CTTGGCCAAA TCGTGATCGA TTGATACTCG CATCTATAAG      60

ATGGCACAGA TCGACTCTTG ATTCACAGAC ATCCGTCAGC CCTCAAGCCG TTTGCAAGTC     120

CACAAACACA AGCACAAGCA TAGCGTCGCA ATGAAGTTCC TTCAAGTCCT CCCTGCCCTC     180

ATACCGGCCG CCCTGGCCCA AACCAGCTGT GACCAGTGGG CAACCTTCAC TGGCAACGGC     240

TACACAGTCA GCAACAACCT TTGGGGAGCA TCAGCCGGCT CTGGATTTGG CTGCGTGACG     300

GCGGTATCGC TCAGCGGCGG GGCCTCCTGG CACGCAGACT GGCAGTGGTC CGGCGGCCAG     360

AACAACGTCA AGTCGTACCA GAACTCTCAG ATTGCCATTC CCAGAAGAG GACCGTCAAC      420

AGCATCAGCA GCATGCCCAC CACTGCCAGC TGGAGCTACA GCGGGAGCAA CATCCGCGCT     480

AATGTTGCGT ATGACTTGTT CACCGCAGCC AACCCGAATC ATGTCACGTA CTCGGGAGAC     540

TACGAACTCA TGATCTGGTA AGCCATAAGA AGTGACCCTC CTTGATAGTT TCGACTAACA     600

ACATGTCTTG AGGCTTGGCA AATACGGCGA TATTGGGCCG ATTGGGTCCT CACAGGGAAC     660

AGTCAACGTC GGTGGCCAGA GCTGGACGCT CTACTATGGC TACAACGGAG CCATGCAAGT     720

CTATTCCTTT GTGGCCCAGA CCAACACTAC CAACTACAGC GGAGATGTCA AGAACTTCTT     780
```

```
CAATTATCTC CGAGACAATA AAGGATACAA CGCTGCAGGC CAATATGTTC TTAGTAAGTC      840

ACCCTCACTG TGACTGGGCT GAGTTTGTTG CAACGTTTGC TAACAAAACC TTCGTATAGG      900

CTACCAATTT GGTACCGAGC CCTTCACGGG CAGTGGAACT CTGAACGTCG CATCCTGGAC      960

CGCATCTATC AACTAAAACC TGGAAACGTG AGATGTGGTG GGCATACGTT ATTGAGCGAG     1020

GGAAAAAAAG CATTGGATCC ATTGAAGATG                                      1050
```

(2) INFORMATION FOR SEQ ID NO:2:

(i) SEQUENCE CHARACTERISTICS:
        (A) LENGTH: 136 amino acids
        (B) TYPE: amino acid
        (C) STRANDEDNESS: single
        (D) TOPOLOGY: linear (xi) SEQUENCE DESCRIPTION: SEQ ID NO:2:

```
Met Lys Phe Leu Gln Val Leu Pro Ala Leu Ile Pro Ala Ala Leu Ala
 1               5                  10                  15

Gln Thr Ser Cys Asp Gln Trp Ala Thr Phe Thr Gly Asn Gly Thr Thr
                20                  25                  30

Val Ser Asn Asn Leu Trp Gly Ala Ser Ala Gly Ser Gly Phe Gly Cys
            35                  40                  45

Val Thr Ala Val Ser Leu Ser Gly Gly Ala Ser Trp His Ala Asp Trp
50                  55                  60

Gln Trp Ser Gly Gly Gln Asn Asn Val Lys Ser Tyr Gln Asn Ser Gln
65                  70                  75                  80

Ile Ala Ile Pro Gln Lys Arg Thr Val Asn Ser Ile Ser Ser Met Pro
                85                  90                  95

Thr Thr Ala Ser Trp Ser Tyr Ser Gly Ser Asn Ile Arg Ala Asn Val
            100                 105                 110

Ala Tyr Asp Leu Phe Thr Ala Ala Asn Pro Asn His Val Thr Tyr Ser
            115                 120                 125

Gly Asp Tyr Glu Leu Met Ile Trp
            130                 135
```

(2) INFORMATION FOR SEQ ID NO:3:

(i) SEQUENCE CHARACTERISTICS:
        (A) LENGTH: 73 amino acids
        (B) TYPE: amino acid
        (C) STRANDEDNESS: single
        (D) TOPOLOGY: linear (xi) SEQUENCE DESCRIPTION: SEQ ID NO:3:

```
Leu Gly Lys Tyr Gly Asp Ile Gly Pro Ile Gly Ser Ser Gln Gly Thr
 1               5                  10                  15

Val Asn Val Gly Gly Gln Ser Trp Thr Leu Tyr Tyr Gly Tyr Asn Gly
                20                  25                  30

Ala Met Gln Val Tyr Ser Phe Val Ala Gln Thr Asn Thr Thr Asn Tyr
            35                  40                  45

Ser Gly Asp Val Lys Asn Phe Phe Asn Tyr Leu Arg Asp Asn Lys Gly
50                  55                  60

Tyr Asn Ala Ala Gly Gln Tyr Val Leu
65                  70
```

(2) INFORMATION FOR SEQ ID NO:4:

(i) SEQUENCE CHARACTERISTICS:
        (A) LENGTH: 25 amino acids (B) TYPE: amino acid
(C) STRANDEDNESS: single
(D) TOPOLOGY: linear (xi) SEQUENCE DESCRIPTION: SEQ ID NO:4:

Ser Tyr Gln Phe Gly Thr Glu Pro Phe Thr Gly Ser Gly Thr Leu Asn
1               5                   10                  15

Val Ala Ser Trp Thr Ala Ser Ile Asn
            20                  25

(2) INFORMATION FOR SEQ ID NO:5:

(i) SEQUENCE CHARACTERISTICS:
        (A) LENGTH: 246 base pairs
        (B) TYPE: nucleic acid
        (C) STRANDEDNESS: single
        (D) TOPOLOGY: linear (xi) SEQUENCE DESCRIPTION: SEQ ID NO:5:

CGCCAATTTG GTACCGAGCC CTTCACGGGC AGTGGAACTC TGAACGTCGC ATCCTGGACC     60

GCATCTATCA ACCCCGGCGG AAACCGTGGC ACCACCACCA CCCGCCGCCC AGCCACTACC    120

ACTGGAAGCT CTCCCGGACC TACCCAGTCT CAAACCAGCT GTGACCAGTG GGCAACCTTC    180

ACTGGCAACG GCTACACAGT CAGCAACAAC CTTTGGGGAG CATCAGCCGG CTCTGAATTC    240

GGCTGC                                                               246

(2) INFORMATION FOR SEQ ID NO:6:

(i) SEQUENCE CHARACTERISTICS:
        (A) LENGTH: 77 amino acids
        (B) TYPE: amino acid
        (C) STRANDEDNESS: single
        (D) TOPOLOGY: linear (xi) SEQUENCE DESCRIPTION: SEQ ID NO:6:

Gln Phe Gly Thr Glu Pro Phe Thr Gly Ser Gly Thr Leu Asn Val Ala
1               5                   10                  15

Ser Trp Thr Ala Ser Ile Asn Pro Gly Gly Asn Arg Gly Thr Thr Thr
            20                  25                  30

Thr Arg Arg Pro Ala Thr Thr Thr Gly Ser Ser Pro Gly Pro Thr Gln
        35                  40                  45

Ser Gln Thr Ser Cys Asp Gln Trp Ala Thr Phe Thr Gly Asn Gly Tyr
    50                  55                  60

Thr Val Ser Asn Asn Leu Trp Gly Ala Ser Ala Gly Ser
65                  70                  75

(2) INFORMATION FOR SEQ ID NO:7:

(i) SEQUENCE CHARACTERISTICS:
        (A) LENGTH: 61 base pairs
        (B) TYPE: nucleic acid
        (C) STRANDEDNESS: single
        (D) TOPOLOGY: linear (xi) SEQUENCE DESCRIPTION: SEQ ID NO:7:

AATTCCGCGG ACTGGCATCA TGAAGTTCCT TCAAGTCCTC CCTGCCCTCA TACCGGCGCC     60

C                                                                    61

(2) INFORMATION FOR SEQ ID NO:8:

(i) SEQUENCE CHARACTERISTICS:
        (A) LENGTH: 55 base pairs
        (B) TYPE: nucleic acid (C) STRANDEDNESS: single
        (D) TOPOLOGY: linear (xi) SEQUENCE DESCRIPTION: SEQ ID NO:8:

CGGCCGGTAT GAGGGCAGGG AGGACTTGAA GGAACTTCAT GATGCCAGTC CGCGG          55

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:9:

CGCCAATTTG GTACCGAGCC CTTCACGGG          29

(2) INFORMATION FOR SEQ ID NO:10:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:10:

GCCACGGTTT CCGCCGGGGT TGATAGATGC GGTCCAGG          38

(2) INFORMATION FOR SEQ ID NO:11:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (xi) SEQUENCE DESCRIPTION: SEQ ID NO:11:

CCTGGACCGC ATCTATCAAC CCCGGCGGAA ACCGTGGC          38

(2) INFORMATION FOR SEQ ID NO:12:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:12:

CCACTGGTCA CAGCTGGTTT GAGACTGGGT AGGTCCGGG          39

(2) INFORMATION FOR SEQ ID NO:13:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:13:

CCCGGACCTA CCCAGTCTCA AACCAGCTGT GACCAGTGG          39

(2) INFORMATION FOR SEQ ID NO:14:

(i) SEQUENCE CHARACTERISTICS:
        (A) LENGTH: 30 base pairs
        (B) TYPE: nucleic acid
        (C) STRANDEDNESS: single
        (D) TOPOLOGY: linear

```
        (xi) SEQUENCE DESCRIPTION: SEQ ID NO:14:

GCAGCCGAAT TCAGAGCCGG CTGATGCTCC                                            30

(2) INFORMATION FOR SEQ ID NO:15:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (xi) SEQUENCE DESCRIPTION: SEQ ID NO:15:

CGCCAATTTG GTACCGAGCC CTTCACGGG                                             29

(2) INFORMATION FOR SEQ ID NO:16:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (xi) SEQUENCE DESCRIPTION: SEQ ID NO:16:

GCAGCCGAAT TCAGAGCCGG CTGATGCTCC                                            30
```